(12) United States Patent
Jones

(10) Patent No.: US 7,168,631 B2
(45) Date of Patent: Jan. 30, 2007

(54) EMANATOR DEVICE

(75) Inventor: Stuart Michael Ruan Jones, Lockington (GB)

(73) Assignee: Reckitt Benckiser (UK) Limited, Slough (GB)

( * ) Notice: Subject to any disclaimer, the term of this patent is extended or adjusted under 35 U.S.C. 154(b) by 208 days.

(21) Appl. No.: 10/399,839

(22) PCT Filed: Oct. 19, 2001

(86) PCT No.: PCT/GB01/04691

§ 371 (c)(1),
(2), (4) Date: Oct. 13, 2003

(87) PCT Pub. No.: WO02/34302

PCT Pub. Date: May 2, 2002

(65) Prior Publication Data

US 2004/0060997 A1 Apr. 1, 2004

(30) Foreign Application Priority Data

Oct. 23, 2000 (GB) ................................. 0025887.1

(51) Int. Cl.
*A24F 25/00* (2006.01)
(52) U.S. Cl. ............................ 239/45; 239/44; 239/34; 239/145; 239/326
(58) Field of Classification Search .................. 239/34, 239/44, 46, 51.5, 6, 45, 51, 326
See application file for complete search history.

(56) References Cited

U.S. PATENT DOCUMENTS

| | | | | |
|---|---|---|---|---|
| 1,939,837 A | * | 12/1933 | Ward .......................... | 239/51.5 |
| 2,283,028 A | * | 5/1942 | Bailey ......................... | 239/45 |
| 3,617,035 A | * | 11/1971 | Hoeher ........................ | 261/99 |
| 4,913,350 A | | 4/1990 | Purzycki | |
| 5,000,383 A | | 3/1991 | Van Der Heijden | |

(Continued)

FOREIGN PATENT DOCUMENTS

EP 1031446 A1 8/2000

(Continued)

OTHER PUBLICATIONS

Combined Search and Examination Report dated Apr. 2, 2001 from The Patent Office in Great Britain for application GB 0025887.1.

(Continued)

*Primary Examiner*—Dinh Q. Nguyen
(74) *Attorney, Agent, or Firm*—Norris McLaughlin & Marcus, PA

(57) ABSTRACT

An emanator for emanating a composition into its surroundings, the emanator comprising: a container for containing a volatile liquid comprising a composition to be emanated; an emanation surface from which the volatile liquid evaporates; a wick for transporting the volatile liquid from the container to the emanation surface, characterized in that the transport of the liquid through both the wick and the emanator occurs at the surface of both the wick and the emanator and in that transport of the liquid through the wick occurs only at the surface of the wick by capillary action. In a preferred embodiment the wick and the emanation system are integrally formed from a material formed with microgrooves.

11 Claims, 1 Drawing Sheet

U.S. PATENT DOCUMENTS

| | | | |
|---|---|---|---|
| 5,810,265 A * | 9/1998 | Cornelius et al. | 239/690 |
| 5,857,620 A | 1/1999 | Nakoneczny | |
| 5,875,968 A | 3/1999 | Miller et al. | |
| 6,275,651 B1 | 8/2001 | Voit | |
| 6,708,897 B1 * | 3/2004 | Hart et al. | 239/45 |

FOREIGN PATENT DOCUMENTS

| | | |
|---|---|---|
| GB | 2333233 A | 7/1999 |
| GB | 2345494 A | 7/2000 |
| GB | 2 355 200 | 4/2001 |
| GB | 2 357 973 A | 7/2001 |

OTHER PUBLICATIONS

Search Report dated Apr. 19, 2002 from The Patent Office in Great Britain for application GB 0125117.2.

PCT Written Opinion dated Jul. 23, 2002 for application PCT/GB01/04691.

Response to PCT Written Opinion dated Oct. 23, 2002 for application PCT/GB01/04691.

PCT International Search Report, dated Feb. 21, 2002, for PCT/GB01/04652.

* cited by examiner

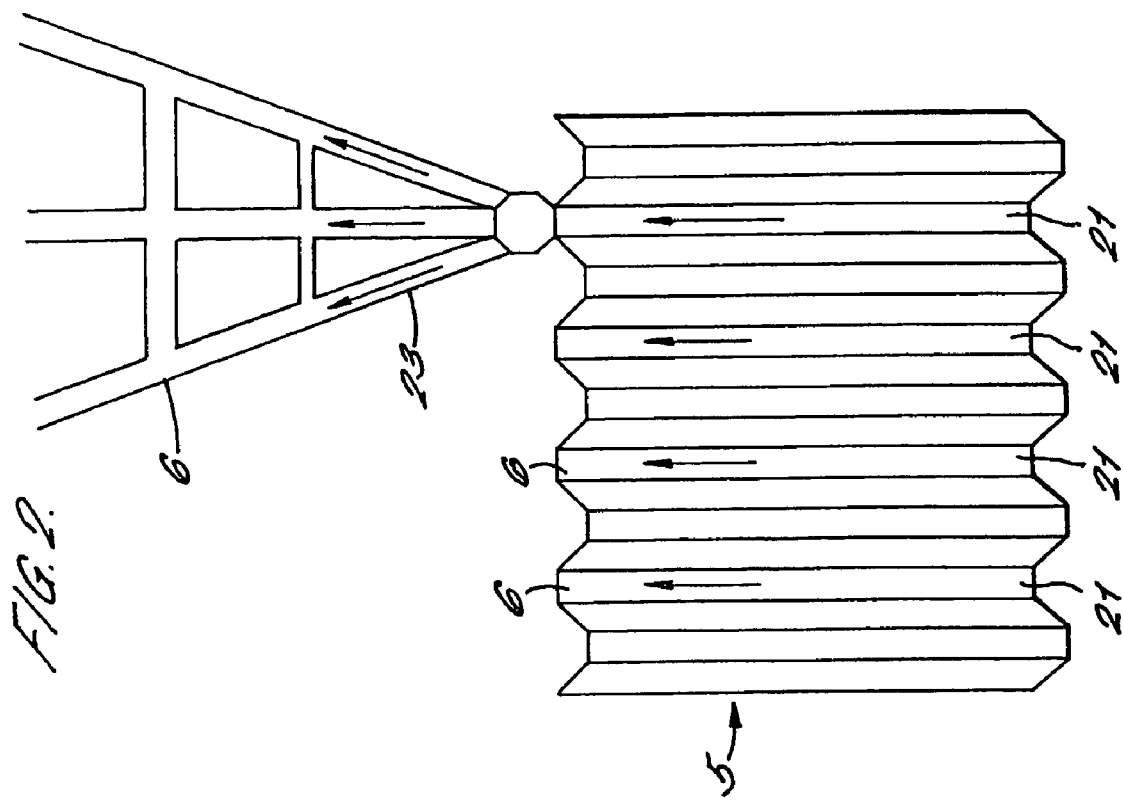
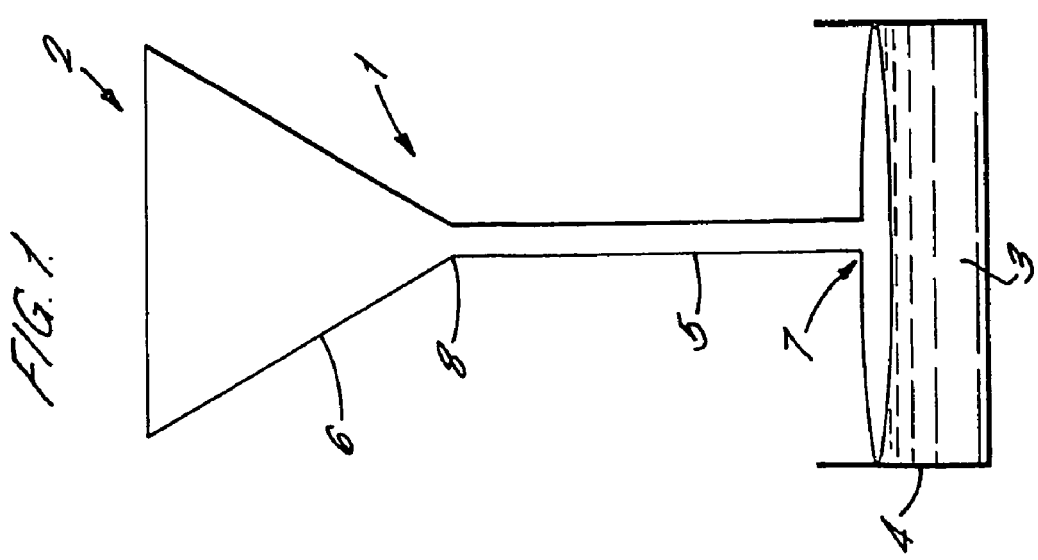

EMANATOR DEVICE

This invention relates to a wick and emanation surface, and particularly, but not exclusively, to a wick and emanation surface for use in an insecticidal device or an air freshener.

A particular type of insecticidal device or air freshener is known as an emanator. An emanator comprises a container in which a reservoir of volatile liquid is contained. The volatile liquid contains within it additives in the form of insecticidal compositions, if the device is an insecticidal device, or fragrance compositions, if the device is an air freshener. The device further comprises an emanation surface, from which the volatile liquid evaporates into its surroundings, and a wick extending from the reservoir to the emanation surface, for transporting the liquid from the reservoir to the emanation surface for evaporation. Evaporation of the liquid results in the fragrance or insecticidal compositions being released into the surroundings.

For the sake of clarity the term air freshener will be used herein to refer to insecticidal devices as well as air fresheners, and the term fragrance composition will be used herein to refer to insecticidal compositions as well as fragrance compositions.

Known wicks for use in emanators typically comprise a bundle of fibres loosely twisted, or a braided or woven cord, tape or tube, which draws up by capillary action the liquid in the reservoir and transports it to the emanation surface where it evaporates.

Wicks may also be made from non-woven material, and porous polymer materials such as sintered plastics may also be used.

A disadvantage of known emanators is that it is necessary to use a separate wick and emanation surface. This is because in order for a capillary action in a wick to effectively and efficiently draw up liquid from the reservoir to the emanating surface, it is necessary for a large void volume to exist within the capillary structure within the wick. Such a void structure does not, however, produce an efficient emanation surface.

A further disadvantage is that the structure of one or both of these components will vary from piece to piece due to manufacturing processes.

According to the first aspect of the present invention there is provided an emanator for emanating a composition into its surroundings, the emanator comprising:

a container for containing a volatile liquid comprising a composition to be emanated;

an emanation surface from which the volatile liquid evaporates;

a wick for transporting the volatile liquid from the container to the emanation surface, characterised in that the transport of the liquid through both the wick and the emanator occurs at the surface of both the wick and the emanator and in that transport of the liquid through the wick occurs only at the surface of the wick.

According to a second aspect of the present invention, there is provided an emanator for emanating a composition into the surroundings, the emanator comprising:

a container for containing a volatile liquid comprising a composition to be emanated;

an emanation surface from which the volatile liquid evaporates;

a wick for transporting the volatile liquid from the container to the emanation surface, characterised in that the wick and the emanation surface are integrally formed, and in that the wick transports the liquid from the container to the emanation surface only by means of capillary action at the surface of the wick.

The combined wick and emanation surface will be referred to herein as the wicking and emanation system.

By having the wick and the emanation surface integrally formed, the device is simpler and therefore cheaper to manufacture and assemble, and will allow improved consistency across and within the batch production.

Advantageously, the wicking and emanation system is formed from a material formed with microgrooves. The term microgroove means a groove heaving a width measured in micrometers, or sub-micrometers. The grooves may have any suitable cross-sectional shape, such a semi-circular or rectangular, triangular or frusto-triangular in cross-section. A material formed with microgrooves may be described as being micro-structured or having a micro-structure.

The microgrooves act as capillaries, and are subdivided or geometrically varied at the emanation surface to provide an extensive area for evaporation.

The wicking and emanation system may be made from any material that is capable of being formed into microgrooves, but preferably the system is formed from a thermoplastics based material.

A method of forming a microstructure is described in International patent application No. PCT/US99/01566 field by Minnesota Mining and Manufacturing Company.

It is known from this patent application, that materials such as acrylates or urathane are suitable for forming an illuminating device, i.e. a light guide having one or more output portions arranged in such a fashion as to provide a desired pattern of illumination at a desired intensity. The materials are used to form a microstructure which in turn forms the illuminating device.

The present inventors have made the surprising discovery that a microstructure may be used as a wicking and emanation device in emanators of the type described herein. The materials described and discussed in WO 99/42270 would not be suitable for use as a combined wick/emanator. This is because materials such as acrylates and urathane would react with fragrances in the volatile liquid to be emanated and stress-cracking would occur.

It is known in the filed that fragrances or insecticidal actives tend to be particularly aggressive towards certain types of polymers. The fragrances or insecticidal actives are capable of reacting with these types of polymers and breaking down the molecular structures of the polymers causing stress cracking to occur.

Suitable materials would therefore be ones which resist attack from the fragrances or insecticidal actives such as polyolefins and PETG which stands for polyethyltetraphalateglycol.

A whole range of materials are likely to be suitable for forming the microstructure. For the present invention it is important to be able to choose a material which is chemically resistant to the fragrances to be used and has a relatively low cost.

Preferably, the wick portion of the system comprises material having a microstructure in the form of substantially parallel grooves, each having a width in the range of 50 microns–750 microns and positioned adjacent one another.

It has been found that microgrooves having a diameter of 50 microns to 750 microns, subject to surface tensions and product viscosity, produce a material having particularly good capillary action.

Advantageously, the emanation portion of the system comprises a microstructure comprising microgrooves which fan out from the wicking microgrooves to form an emanation surface having a surface area to volume ratio that is large.

For the emanation surface to perform effectively in the emanation of the liquid, it is necessary for there to be a large surface area to volume ratio in the range 5:1 to 100:1. The larger the surface are the higher the emanation rate by the process of surface air flow. The shallower the channels the more efficient the fragrance volume to fragrance release. There is of course a limit to the optimum ratio of surface area to volume, in that in an extreme situation, where there was virtually no depth of liquid, surface tension would have an adverse effect on the emanation of the liquid.

Ideally the rate of wicking and emanation should be matched for optimization. The particular size and geometry of the grooves will depend upon the volatility of the fragrances used in the volatile liquid, however, for most applications, the release rate of the fragrance should be in the order of 0.1 $cm^3$ to 10 $cm^3$ per day. The size and geometry of the structure will therefore be calculated to result in a rate of release within this range. The emanator grooves are repositioned relative to the wicking grooves such that their depth is minimised and their surface area maximised within the constraints of fragrance transport.

An advantage of using a microstructure to form the wicking and emanation system is that the transport of liquid is a surface transport and therefore absorption of the liquid into the system is minimal, if not non existent, thus improving evaporation efficiencies from the surface and reducing fragrance capture as experienced with absorption pads.

The invention will now be further described by way of example only with reference to the accompanying drawings in which:

FIG. 1 is a schematic representation of a wicking and emanation system according to the present invention; and FIG. 2 is a schematic representation of the wicking and emanation system of FIG. 1 showing the microstructure of the system.

Referring to FIG. 1 a wicking and emanation system according to the present invention is designated generally by the reference 1. The wicking and emanation system forms part of an emanator which may be used as an air freshener or insecticidal device. For the sake of clarity the present example will be described in terms of an air freshener.

The device incorporating the wicking and emanation system will be referred to by reference numeral (2). The emanator (2) comprises a liquid reservoir (3) formed in a container (4). The wicking and emanation system (1), comprises a wicking portion (5) and an emanation system (6). The wicking portion (5) has an end (7) remote from the emanation surface, which end is in contact with the liquid (3). Liquid from the liquid reservoir (3) is drawn up the wick portion (5) of the wicking and emanation system (1) by means of capillary action.

When the liquid reaches the junction (8) between the wick portion (5) and the emanation surface (6) it is drawn into the emanation surface (6) also by capillary action to provide an extended surface area. Efficient evaporation can then occur from the emanation surface (6).

The liquid contained in the reservoir (3) comprises a volatile liquid in which chemical additives have been added. The additives are in the form of fragrances which are released into the atmosphere when the liquid evaporates at the emanation surface.

Referring now to figure (2), the microstructure of the wicking and emanation system (1) is shown. The wicking portion (5) comprises a plurality of grooves (21) positioned adjacent one another. The cross-section of the grooves is frusto-triangular, although any other suitable shape could be used. Liquid from the reservoir (3) is drawn up the grooves (21) by capillary action towards the emanation surface (6). At the emanation surface each groove (21) divides into a plurality of grooves (23), in this case three grooves. For the sake of clarity the grooves forming the emanation surface (6) have been shown extending from one groove (21) only. However, in reality similar structures would extend from each groove (21) providing an extended surface area from which the fragrance can evaporate.

The invention claimed is:

1. An emanator for emanating a composition into its surroundings, the emanator comprising:
   a container for containing a volatile liquid comprising a composition to be emanated;
   an emanation surface from which the volatile liquid evaporates;
   a wick for transporting the volatile liquid from the container to the emanation surface,
   characterized in that the transport of the liquid through both the the wick and the emanator occurs at the surface of both the wick and the emanator and in that transport of the liquid through the wick occurs only at the surface of the wick, and in that the wicking and emanation system is formed from a material formed with microgrooves, wherein said microgrooves are subdivided or geometrically varied at the emanation surface to provide an extensive surface for evaporation.

2. An emanator far emanating a composition into the surroundings, the emanator comprising:
   a container for containing a volatile liquid comprising a composition to be emanated;
   an emanation surface from which the volatile liquid evaporates;
   a wick for transporting the volatile liquid from the container to the emanation surface,
   characterized in that the wick and the emanation surface are integrally formed, in that the wick transports the liquid from the container to the emanation surface only by means of capillary action at the surface of the wick, and in that the wicking and emanation system is formed from a material formed with microgrooves, wherein said microgrooves are subdivided or geometrically varied at the emanation surface to provide an extensive surface for evaporation.

3. An emanator according to claim 1 wherein the wicking and emanation system is formed from a polyolefin.

4. An emanator according to claim 1 wherein the wick portion of the emanation system comprises material having a microstructure in the form of substantially parallel grooves, each having a width in the range of 50 microns to 750 microns and positioned adjacent one another.

5. An emanator according to claim 1 wherein the emanation portion of the system comprises a microstructure comprising microgrooves which fan out from the wicking microgrooves to form an emanation surface having a surface area to volume ratio that is large.

6. An emanator according to claim 1 wherein the rate emanation a composition into its surroundings is from 0.1 $cm^3$ to 10 $cm^3$ per day of the composition.

7. An emanator according to claim 2 wherein the wicking and emanation system is formed from a polyolefin.

8. An emanator according to claim 2 wherein the wick portion of the emanation system comprises material having a microstructure in the form of substantially parallel grooves, each having a width in the range of 50 microns to 750 microns and positioned adjacent one another.

9. An emanator according to claim 2 wherein the emanation portion of the system comprises a microstructure comprising microgrooves which fan out from the wicking microgrooves to form an emanation surface having a surface area to volume area that is large.

10. An emanator according to claim 2 wherein the rate emanation a composition into its surroundings is from 0.1 cm$^3$ to 10 cm$^3$ per day of the composition.

11. An emanator according to claim 5 wherein the surface area to volume ration is about 5:1 to about 100:1.

* * * * *